United States Patent

Smith et al.

[11] Patent Number: 5,160,658
[45] Date of Patent: Nov. 3, 1992

[54] SURFACTANT COMPOSITIONS

[75] Inventors: Kim R. Smith; James E. Borland; Terry Crutcher; Joe D. Sauer, all of Baton Rouge, La.

[73] Assignee: Ethyl Corporation, Richmond, Va.

[21] Appl. No.: 788,814

[22] Filed: Nov. 7, 1991

[51] Int. Cl.$^5$ ............................................... C11D 1/18
[52] U.S. Cl. ............................. 252/174.19; 252/547; 252/DIG. 5; 252/DIG. 13; 252/DIG. 14; 424/70
[58] Field of Search ............ 252/174.19, 547, DIG. 5, 252/DIG. 13, DIG. 14; 424/70

[56] References Cited

U.S. PATENT DOCUMENTS 3,914,185 10/1975 Inamorato .......................... 252/547
4,832,872 5/1989 Scandel .............................. 252/547

*Primary Examiner*—Patrick P. Garvin
*Assistant Examiner*—E. D. Irzinski
*Attorney, Agent, or Firm*—Patricia J. Hogan

[57] ABSTRACT

Surfactant mixtures which have better formability than the individual components consist of 55-95% by weight of an amine oxide corresponding to the formula RR'R"NO in which R is a primary alkyl group containing 6-24 carbons R' and R" are independently selected from methyl, ethyl, and 2-hydroxyethyl and 45-5% by weight of an alkylphenoxysulfosuccinate in which the alkyl group contains 8-18 carbons. Preferred mixtures are those in which the amine oxide is N-tetradecyldimethylamine oxide and the alkylphenoxysulfosuccinate is nonylphenoxysulfosuccinate.

5 Claims, No Drawings

SURFACTANT COMPOSITIONS

FIELD OF INVENTION

This invention relates to surfactant compositions and more particularly to such compositions which are mixtures of amine oxides and sulfosuccinates.

BACKGROUND

It is known that various surfactants have been found to be useful in cleaning compositions, such as shower gels, shampoos, and light duty detergents (e.g., dish detergents)—compositions in which good foamability is a prerequisite for consumer approval. The surfactants which have been used to the greatest extent in such compositions are anionic surfactants, such as alkyl sulfates, alkyl ether sulfates, sulfonates, sulfosuccinates, and sarcosinates.

Although the use of anionic surfactants in these compositions permits the attainment of desirable characteristics, including good foamability, it would be beneficial to find other surfactants which could provide equal or better performance at a lower cost. However, other known surfactants, such as amine oxides, betaines, and alkanolamides, are either more costly than the anionic surfactants or give poorer performance, e.g., smaller foam volume, when substituted for the anionic surfactants.

It is sometimes advantageous to use mixtures of surfactants in cleaning compositions when the surfactants can serve different functions, e.g., one serving to improve foamability and another serving to adjust viscosity. However, known surfactant mixtures typically provide a compromise between what can be achieved with the surfactant ingredients alone. Thus, e.g., a mixture of (A) a more costly surfactant which provides good foamability by itself with (B) a less expensive surfactant which provides poorer foamability by itself will provide an intermediate foamability.

SUMMARY OF INVENTION

It has been found that a mixture of 55–95% by weight of an amine oxide corresponding to the formula RR'R"NO in which R is a primary alkyl group containing 6–24 carbons and R' and R" are independently selected from methyl, ethyl, and 2-hydroxyethyl and 45–5% by weight of an alkylphenoxysulfosuccinate in which the alkyl group contains 8–18 carbons provides more foam than the individual components of the surfactant mixture.

DETAILED DESCRIPTION

Amine oxides which can be used in the practice of the invention are compounds corresponding to the formula RR'R"NO in which R is a primary alkyl group containing 6–24 carbons, preferably 10–18 carbons, and R' and R" are independently selected from methyl, ethyl, and 2-hydroxyethyl. The preferred amine oxides are those in which the primary alkyl group has a straight chain in at least most of the molecules, generally at least 70%, preferably at least 90% of the molecules; and the amine oxides which are especially preferred are those in which R contains 10–18 carbons and R' and R" are both methyl.

Exemplary of the preferred amine oxides are the N-hexyl-, N-octyl-, N-decyl-, N-dodecyl-, N-tetradecyl-, N-hexadecyl-, N-octadecyl-, N-eicosyl-, N-docosyl-, and N-tetracosyldimethylamine oxides, the corresponding amine oxides in which one or both of the methyl groups are replaced with ethyl or 2-hydroxyethyl groups, etc., and mixtures thereof. A particularly preferred amine oxide is N-tetradecyldimethylamine oxide.

The alkylphenoxysulfosuccinates which may be used in admixture with the amine oxides are those in which the alkyl group contains 8–18 carbons. A particularly preferred sulfosuccinate is nonylphenoxysulfosuccinate.

The amine oxide/sulfosuccinate mixtures of the invention are synergistic in all proportions and provide foam levels higher than can be achieved by the use of either component alone. Optimum foamability is obtained when the mixtures contain 60–90%, most preferably 70–80% by weight of the amine oxide.

The invention is advantageous in that it provides novel surfactant mixtures which can provide acceptable levels of foam more economically than the individual components of the mixtures. This characteristic of the mixtures makes them valuable for use in the cleaning compositions which require foaming for customer approval, e.g., shampoos, shower gels, and light duty detergents.

When employed in such compositions, the surfactant mixtures are utilized in an aqueous medium, which typically constitutes about 10–90% of the weight of the compositions; and they may be used in conjunction with other ingredients of the types conventionally used in the compositions. Such ingredients include, e.g., viscosity improvers, pH adjusters, colorants, pearlizing agents, clarifying agents, fragrances, preservatives, antioxidants, chelating agents, skin and hair conditioners, botanical extracts, and antibacterial agents.

The following example is given to illustrate the invention and is not intended as a limitation thereof. Unless otherwise specified, quantities mentioned in the example are quantities by weight.

EXAMPLE

Dissolve varying amounts of N-tetradecyldimethylamine oxide and nonylphenoxysulfosuccinate (NPSS) in hard water (200 ppm as $CaCO_3$) to provide solutions having a total surfactant content of 0.1%. Measure the foamability of the surfactants by (1) placing 30 mL of each of the solutions in a 100 mL stoppered graduated cylinder, (2) inverting the cylinder ten times, (3) measuring the foam height, (4) repeating steps 1–3 twice, and (5) calculating the average of the three measurements. The proportions of amine oxide and NPSS used in preparing each of the solutions and the foam heights obtained from them are shown in the table below.

TABLE

| % Amine Oxide | % NPSS | Foam Height (mL) |
| --- | --- | --- |
| 100 | 0 | 33 |
| 75 | 25 | 40 |
| 50 | 50 | 33 |
| 25 | 75 | 33 |
| 0 | 100 | 31 |

What is claimed is:

1. A surfactant mixture consisting of 55–95% by weight of an amine oxide corresponding to the formula RR'R"NO in which R is a primary alkyl group containing 6–24 carbons and R' and R" are independently selected from the group consisting of methyl, ethyl, and 2-hydroxyethyl and 45–5% by weight of an alkylphenoxysulfosuccinate in which the alkyl group contains 8-18 carbons.

2. The surfactant mixture of claim 1 wherein R is a primary alkyl group containing 10-18 carbons and R' and R" are methyl.

3. The surfactant mixture of claim 2 wherein the amine oxide is N-tetradecyldimethylamine oxide and the alkylphenoxysulfosuccinate is nonylphenoxysulfosuccinate.

4. The surfactant mixture of claim 1 containing about 60-90% by weight of the amine oxide.

5. The surfactant mixture of claim 4 containing about 70-80% by weight of the amine oxide.

* * * * *